US 8,839,954 B2

(12) United States Patent
Disch

(10) Patent No.: US 8,839,954 B2
(45) Date of Patent: Sep. 23, 2014

(54) MEDICAL CLIP CARRIER DEVICE

(71) Applicant: Aesculap AG, Tuttlingen (DE)

(72) Inventor: Alexander Disch, Freiburg (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/723,468

(22) Filed: Dec. 21, 2012

(65) Prior Publication Data

US 2013/0161216 A1    Jun. 27, 2013

(30) Foreign Application Priority Data

Dec. 21, 2011   (DE) .......................... 10 2011 056 821

(51) Int. Cl.
  B65D 85/24        (2006.01)
  A61B 17/06        (2006.01)
  A61B 17/122       (2006.01)

(52) U.S. Cl.
  CPC ............ B65D 85/24 (2013.01); A61B 17/1222 (2013.01)
  USPC ........... 206/338; 206/339; 206/340; 206/438; 206/63.3; 606/142; 606/143; 606/151; 606/158

(58) Field of Classification Search
  CPC ............................... B65D 85/24; A61B 17/10
  USPC ......... 206/338–348, 438, 63.3; 606/142, 143, 606/151, 157, 158
  See application file for complete search history.

(56) References Cited

U.S. PATENT DOCUMENTS

| 491,235 | A | * | 2/1893 | Brown .......................... 206/340 |
| 3,363,628 | A | | 1/1968 | Wood |
| 3,713,533 | A | * | 1/1973 | Reimels ........................ 206/339 |
| 4,146,130 | A | | 3/1979 | Samuels et al. |
| 4,212,390 | A | | 7/1980 | Raczkowski et al. |
| 4,361,229 | A | | 11/1982 | Mericle |
| 4,696,396 | A | | 9/1987 | Samuels |
| 4,936,447 | A | | 6/1990 | Peiffer |
| 4,961,499 | A | * | 10/1990 | Kulp ............................. 206/339 |
| 4,972,949 | A | | 11/1990 | Peiffer |
| 5,046,611 | A | * | 9/1991 | Oh ................................ 206/339 |
| 5,046,624 | A | * | 9/1991 | Murphy et al. .............. 211/70.6 |
| 5,201,416 | A | | 4/1993 | Taylor |
| 5,441,509 | A | | 8/1995 | Vidal et al. |
| 5,518,115 | A | * | 5/1996 | Latulippe ..................... 206/370 |
| 5,908,430 | A | | 6/1999 | Appleby |

(Continued)

FOREIGN PATENT DOCUMENTS

DE     690 29 474     7/1997
DE     199 03 752     3/2000

(Continued)

Primary Examiner — Mickey Yu
Assistant Examiner — Gideon Weinerth
(74) Attorney, Agent, or Firm — Lipsitz & McAllister, LLC

(57) ABSTRACT

The invention relates to a medical clip carrier device for retention and/or mounting of at least one medical clip, in particular a ligature clip, comprising at least one clip receptacle in which a clip is retainable in a mounted position, and a securing device with at least one securing member for detachably securing a clip in the at least one clip receptacle. The clip receptacle comprises an insertion opening for insertion of a clip into the clip receptacle and removal of the clip therefrom. The at least one securing member is constructed in the form of a retaining projection which protrudes at least partially into the insertion opening.

19 Claims, 7 Drawing Sheets

(56) References Cited

U.S. PATENT DOCUMENTS

| | | | |
|---|---|---|---|
| 5,913,422 A * | 6/1999 | Cote et al. | 206/370 |
| 6,044,971 A * | 4/2000 | Esposito et al. | 206/339 |
| 6,048,503 A * | 4/2000 | Riley et al. | 422/298 |
| 6,158,583 A | 12/2000 | Forster | |
| 6,273,253 B1 | 8/2001 | Forster et al. | |
| 6,391,260 B1 * | 5/2002 | Davis et al. | 422/28 |
| 6,460,700 B2 | 10/2002 | Weisshaupt | |
| 6,572,819 B1 * | 6/2003 | Wu et al. | 422/28 |
| 6,880,699 B2 | 4/2005 | Gallagher | |
| D557,814 S * | 12/2007 | Glenn et al. | D24/217 |
| 7,628,272 B2 | 12/2009 | Wiedenbein | |
| 8,069,998 B2 * | 12/2011 | Thomas | 211/85.13 |
| 8,079,468 B2 * | 12/2011 | Pleil et al. | 206/339 |
| 8,312,992 B2 | 11/2012 | Disch | |
| 8,403,138 B2 * | 3/2013 | Weisshaupt et al. | 206/340 |
| 8,627,955 B2 * | 1/2014 | Weisshaupt et al. | 206/340 |
| 2002/0017472 A1 | 2/2002 | Weisshaupt | |
| 2002/0046961 A1 * | 4/2002 | Levinson et al. | 206/339 |
| 2005/0029142 A1 * | 2/2005 | Nordquist | 206/438 |
| 2006/0124485 A1 * | 6/2006 | Kennedy | 206/340 |
| 2006/0212049 A1 * | 9/2006 | Mohiuddin | 606/151 |
| 2007/0212277 A1 * | 9/2007 | Riley | 422/292 |
| 2008/0272012 A1 | 11/2008 | Stopek | |
| 2008/0312670 A1 * | 12/2008 | Lutze et al. | 606/157 |
| 2011/0087244 A1 | 4/2011 | Weisshaupt et al. | |
| 2011/0108446 A1 * | 5/2011 | Bettenhausen et al. | 206/438 |
| 2011/0144662 A1 * | 6/2011 | McLawhorn et al. | 606/142 |
| 2011/0297571 A1 * | 12/2011 | Brand | 206/438 |
| 2012/0234781 A1 * | 9/2012 | Cogliano et al. | 211/85.13 |
| 2013/0140206 A1 * | 6/2013 | Weisshaupt et al. | 206/339 |

FOREIGN PATENT DOCUMENTS

| | | |
|---|---|---|
| DE | 101 05 235 | 8/2002 |
| DE | 697 13 608 | 2/2003 |
| DE | 20 2006 011 054 | 10/2006 |
| DE | 10 2006 001 344 | 7/2007 |
| DE | 20 2007 007 097 | 8/2007 |
| DE | 20 2008 004 929 | 7/2008 |
| DE | 10 2008 018 158 | 10/2009 |
| EP | 0 072 171 | 3/1987 |
| EP | 0 494 243 | 12/1996 |
| EP | 0 482 861 | 3/1997 |

* cited by examiner

MEDICAL CLIP CARRIER DEVICE

CROSS-REFERENCE TO RELATED APPLICATIONS

This application claims the benefit of German application number 10 2011 056 821.2 filed on Dec. 21, 2011, which is incorporated herein by reference in its entirety and for all purposes.

FIELD OF THE INVENTION

The present invention relates to medical clip carrier devices for retention and/or mounting of at least one medical clip generally, and more specifically to a medical clip carrier device for retention and/or mounting of at least one medical clip, in particular a ligature clip, comprising at least one clip receptacle in which a clip is retainable in a mounted position, and a securing device with at least one securing member for detachably securing a clip in the at least one clip receptacle, wherein the clip receptacle comprises an insertion opening for insertion of a clip into the clip receptacle and removal of the clip therefrom.

BACKGROUND OF THE INVENTION

A clip carrier device of the type described in the introduction is known for example in the form of a bearing body described in DE 20 2008 004 929 U1. It serves in particular for mounting substantially C-shaped surgical clips in the form of ligature clamps having two limbs connected to one another by a linking web. Retaining members which can be moved from a retention position into a released position and optionally back again serve to retain the clip on the known bearing body.

Thus such a known bearing body has a comparatively complex construction, as it must be ensured that the retaining members securely retain the clips which are inserted in the clip receptacles. However, when the retaining members are removed they must be pushed away, which in the most unfavourable case can lead to an unwanted deformation of the clip.

In particular, so-called double-shank clips as disclosed in DE 20 2008 004 929 U1 and in DE 10 2006 001 344 A1 are not only very small but also highly sensitive. Any type of unintentional deformation may impair the functioning of the clip.

SUMMARY OF THE INVENTION

In a first aspect of the invention, a medical clip carrier device for retention and/or mounting of at least one medical clip, in particular a ligature clip, comprises at least one clip receptacle in which a clip is retainable in a mounted position, and a securing device with at least one securing member for detachably securing a clip in the at least one clip receptacle. The clip receptacle comprises an insertion opening for insertion of a clip into the clip receptacle and removal of the clip therefrom. The at least one securing member is constructed in the form of a retaining projection which protrudes at least partially into the insertion opening.

BRIEF DESCRIPTION OF THE DRAWING FIGURES

The foregoing summary and the following description may be better understood in conjunction with the drawing figures, of which:

DETAILED DESCRIPTION OF THE INVENTION

Figure 1:
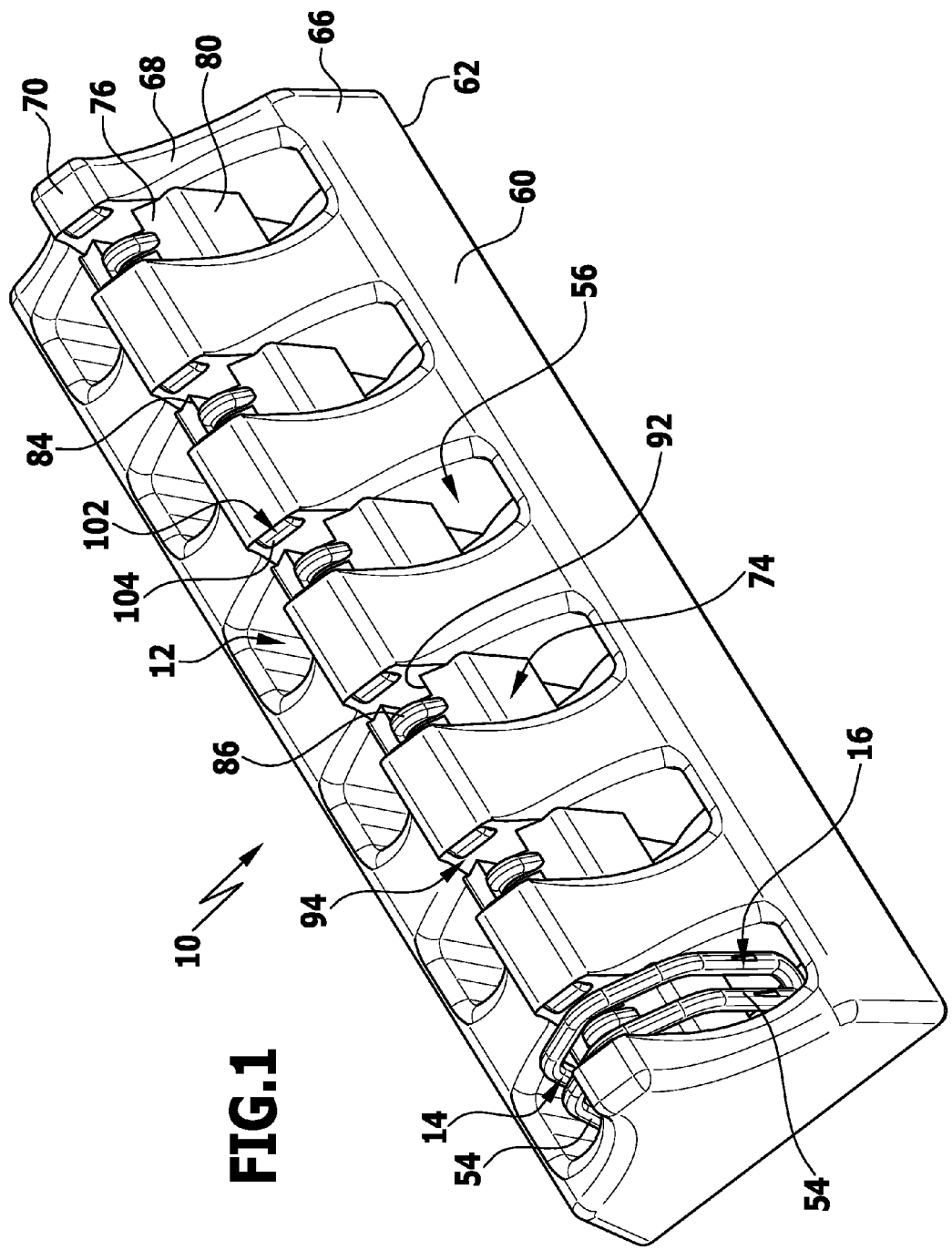
FIG. 1 shows a perspective overall view of a clip carrier device with six clip receptacles, of which one for example is equipped with a surgical double-shank clip.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical clip carrier device for retention and/or mounting of at least one medical clip, in particular a ligature clip, comprising at least one clip receptacle in which a clip is retainable in a mounted position, and a securing device with at least one securing member for detachably securing a clip in the at least one clip receptacle, wherein the clip receptacle comprises an insertion opening for insertion of a clip into the clip receptacle and removal of the clip therefrom, wherein the at least one securing member is constructed in the form of a retaining projection which protrudes at least partially into the insertion opening.

This configuration of the clip carrier device makes it possible in particular to securely mount double-shank clips and to remove them in a simple manner from the clip receptacle. The configuration of the at least one securing member may in particular utilise the special characteristic of a double-shank clip, namely that the two clips which together form the double-shank clip, and are connected to one another at their free ends, are movable towards one another at least to a limited extent in a direction transversely with respect to the closing direction of the retaining arms of the clip. This movability is exploited when the clip is inserted into the clip receptacle past at least one securing member and when the clip is removed from the clip receptacle past at least one securing member. In the actual closing direction of the two retaining or clamping arms of the clip towards one another in conjunction with a clip receptacle constructed in such a way, no deformation of the clip and thus also no damage thereto can occur. The present invention, therefore, provides an improved medical clip carrier device of the type described in the introduction which makes both the mounting and the removal of a clip from the clip carrier device more secure and simpler.

In a particularly simple and secure manner a clip can be retained in a clip receptacle of the clip carrier device and can be secured against falling out if the at least one securing member comprises a retaining face facing in the direction into the clip receptacle. In this way a clip cannot be removed from the clip receptacle without being grasped appropriately by a user and optionally deformed in the direction transversely with respect to the actual clamping direction.

A particularly simple and secure mounting can in particular be achieved if the clip carrier device comprises at least two securing members per clip receptacle.

The structure of the clip carrier device can be further simplified if the at least two securing members are oriented facing one another and narrow the insertion opening. Thus in particular it is possible to prevent a clip from unintentionally falling out of the clip receptacle, even if this latter should be moved in an undefined manner and the clip could fall out of the clip receptacle solely due to the gravity acting on it.

In order to improve a mounting of a clip on the clip carrier device, it is favourable if the clip receptacle comprises at least two support surfaces, against which, in the mounting position, a respective limb of a clip abuts at least in some sections or substantially abuts. A limb of a clip may in particular be a retaining or clamping arm thereof. The at least two support surfaces may ensure that before the application for example to a hollow organ in the form of a blood vessel the clip does not deform unintentionally due to movement of the limbs of the clip towards one another.

Furthermore, the design and the production of the clip carrier device may be simplified in particular by construction of the clip receptacle symmetrically with respect to at least one mirror plane. In particular it may be constructed in mirror symmetry with respect to two mirror planes extending perpendicular to one another.

It is advantageous if the clip receptacle comprises two retaining arm receiving spaces to receive a respective a retaining arm of the clip. This makes it possible in particular to configure a retaining arm receiving space so that a retaining arm of the clip is retained as in a holster. Withdrawal of the retaining arm of the clip from the retaining arm receiving space is prevented in particular by the securing device.

In order to limit an insertion depth of the clip into the clip receptacle, it is favourable if the at least two support surfaces are connected to one another via a contact surface. This makes it possible that, in particular even in the transition region between its retaining or clamping arms, the clip can abut on the contact surface.

It is advantageous if the contact surface is constructed facing in the direction of the insertion opening. Thus the contact surface simultaneously forms a stop face for a transition region of the clip between its retaining or clamping arms and thus a stop for the clip during insertion into the clip receptacle.

According to a further preferred embodiment it may be provided that the contact surface comprises at least one separating element for separating or dividing the contact surface into a first and a second contact surface section. The is particularly favourable if a double-shank clip is to be mounted in the clip receptacle. The separating element may in particular form a stop acting in the transverse direction in order to limit a movement of the two clip halves towards one another in the transition region, also designated as the connection point, between the respective retaining or clamping arms. In this way, during insertion of the clip into the clip receptacle an unwanted, excessive deformation can additionally be avoided or at least limited.

The medical clip carrier device can be configured particularly simply if the at least one separating element is constructed in the form of a separating projection projecting from the contact surface.

The separating projection is advantageously ribbed or constructed in the form of a rib. Such a separating projection can in particular engage between the two clip halves of a double-shank clip which are constructed as brackets in order to hold these clip halves spaced apart from one another in the required manner.

The structure of the clip receptacle of the clip carrier device can in particular be simplified in that the at least one separating element defines a first plane of symmetry which reflects each of the two retaining arm receiving spaces in itself. Thus a clip of correspondingly symmetrical construction can be mounted securely in the clip receptacle of the clip carrier device.

Furthermore it may be advantageous if the at least one separating element defines a second plane of symmetry which reflects the at least one separating element in itself and reflects the one retaining arm receiving space into the other retaining arm receiving space and vice versa. In particular the second plane of symmetry can extend perpendicular to the first plane of symmetry. As a result in particular the construction costs for production of the clip carrier device are minimised.

The contact surface preferably comprises at least one flushing opening. It is advantageous if two flushing openings are provided. In this way it can be ensured that, before or also after it is equipped with one or more clips, the clip carrier device can be cleaned, for example with a cleaning fluid, wherein the cleaning fluid can then run off in a specific manner.

The at least one separating element preferably separates two flushing openings from one another. Thus it can be ensured that a flushing or cleaning fluid for cleaning the clip carrier device can run off securely with or without clips mounted thereon.

In order to prevent fluid from collecting in the clip receptacle, it is advantageous if the clip receptacle comprises at least one outlet opening.

It is advantageous if each retaining arm receiving space comprises an outlet opening. This means that fluids, for example flushing or cleaning fluids, which are used for cleaning the clip carrier device with or without clips retained thereon, can flow off from the respective retaining arm receiving space. In this way there is obtained an improved drying result, for example after hot steam sterilisation, of the clip carrier device with or without clips mounted thereon.

Each outlet opening preferably borders on at least one support surface. This ensures in particular that a fluid can exit directly from the support surface through the outlet opening and can flow off from a clip retained in the clip receptacle.

It is advantageous if the clip carrier device comprises two or more clip receptacles. This makes it possible to construct the clip carrier device for example as a bearing body for a clip magazine which can simultaneously hold two or more clips.

In order to simplify the insertion of a clip, in particular of the retaining or clamping arm thereof into the retaining arm receiving spaces, it is advantageous if each retaining arm receiving space has at least one partially open side face directed away from the clip carrier device. Furthermore, this has the advantage that a clip retained on the clip carrier device can be easily washed by a cleaning fluid.

Furthermore it is advantageous if the clip carrier device is constructed in one piece. Thus it can for example be produced simply and cost-effectively by injection moulding.

The clip carrier device can be produced particularly simply and cost-effectively if it is produced from a plastics material. This may in particular be a plastics material which can be sterilised with steam, such as for example polyether ether ketone.

In order to further improve the production and the handling of the clip carrier device, it is advantageous if the clip carrier device comprises no movable parts. In this way a defined and secure mounting of the clips on the clip carrier device can be achieved. Possible damage to retaining members, such as is possible in a bearing body described in DE 20 2008 004 929 U1, can thus be avoided.

The stability of the clip carrier device can be further increased in particular in that the securing device comprises exclusively rigid, inelastic or substantially inelastic parts. In this context "inelastic" relates in particular to a component produced from a hard plastics material, which is not deformable or substantially not deformable when a clip is inserted into and removed from the clip receptacle. In this case in particular the size of the clips which can only exert minimal forces on the clip carrier device should be taken into consideration.

According to a further preferred embodiment of the invention it may be provided that at least one medical clip is retained in the at least one clip receptacle. This has the advantage that for example a surgeon does not have to fasten the clip to the clip carrier device before a surgical intervention, but can be provided with one or more clips already sterilised and retained on the clip carrier device.

In order to further improve the handling it is advantageous if each clip receptacle is equipped with a clip. This enables a surgeon to remove a plurality of clips successively in a specific and simple manner from the clip carrier device and to apply them to a patient, for example also in conjunction with an application instrument.

It is advantageous if the clip is constructed in the form of a double-shank clip. This makes it possible in the manner already described above to exploit the characteristic of a double-shank clip, namely a certain elasticity in a direction of movement of the two clip halves towards one another, and transversely or substantially transversely with respect to a closing direction of the retaining or clamping arm towards one another.

It is advantageous if the at least one clip comprises two retaining arms which are connected to one another at each end via a deformable connection point and are bendable towards to one another in such a way that the retaining arms are moveable out of an open position in which they have a greater spacing from one another into a closed position in which inner faces, which face towards one another, of the retaining arms are permanently moved close together. Such a clip is highly suitable in order to pinch off hollow organs, for example in the form of blood vessels. Such clips can be used in particular for the treatment of aneurysms.

It is advantageous if the clip is constructed from a self-contained strip part which in the region of the two retaining arms and the connection point comprises two sections which lie adjacent to one another and are connected to one another at the free ends of the retaining arms facing away from the connection point. Such a clip may in particular take the form of a double-shank clip. This enables even more secure pinching off of a hollow organ, since by application of a double-shank clip effectively in one working step two clips are applied simultaneously adjacent to one another at a defined spacing.

It is advantageous if the width of the insertion opening in the region of the securing device is smaller than the spacing between outer side faces of the retaining arms which face away from one another away in the region of the connection point. A consequence of this is that when the clip is inserted into the clip receptacle in particular the retaining arms in the region of the connection point can preferably move towards one another in order to be able to pass the insertion opening. As soon as the securing device is passed in the region of the insertion opening, the retaining arms in the region of the connection point return to their original form and are secured in the clip receptacle by the at least one securing member of the securing device.

It is advantageous if the spacing between side faces, which face away from one another, of the at least one separating element is smaller than the spacing between inner side faces of the retaining arms which face one another in the region of the connection point. This makes it possible in particular to move the retaining arms in the region of the connection point somewhat towards one another, but preferably only so far that the spacing between inner side faces which face one another is not smaller than the spacing between side faces, which are directed away from one another, of the at least one separating element. Thus the separating element can in particular serve as a limit of movement and thus as a stop for movement of the retaining arms towards one another in the region of the connection point.

In order to be able to insert a clip into the clip receptacle in a simple manner it is advantageous if the retaining arms of the at least one clip are movable towards one another in the region of the connection point. In this way the spacing between the retaining arms in the region of the connection point can be reduced, so that insertion through the insertion opening past the securing device is possible.

A medical clip carrier device designated overall by the reference numeral 10 is shown schematically by way of example in FIG. 1, and comprises a total of six clip receptacles, each of which receives a surgical clip 14. It is of course possible to equip the clip carrier device 10 with any other number of clip receptacles 12, for example only one, two, three or in particular also more than six.

Figure 7:
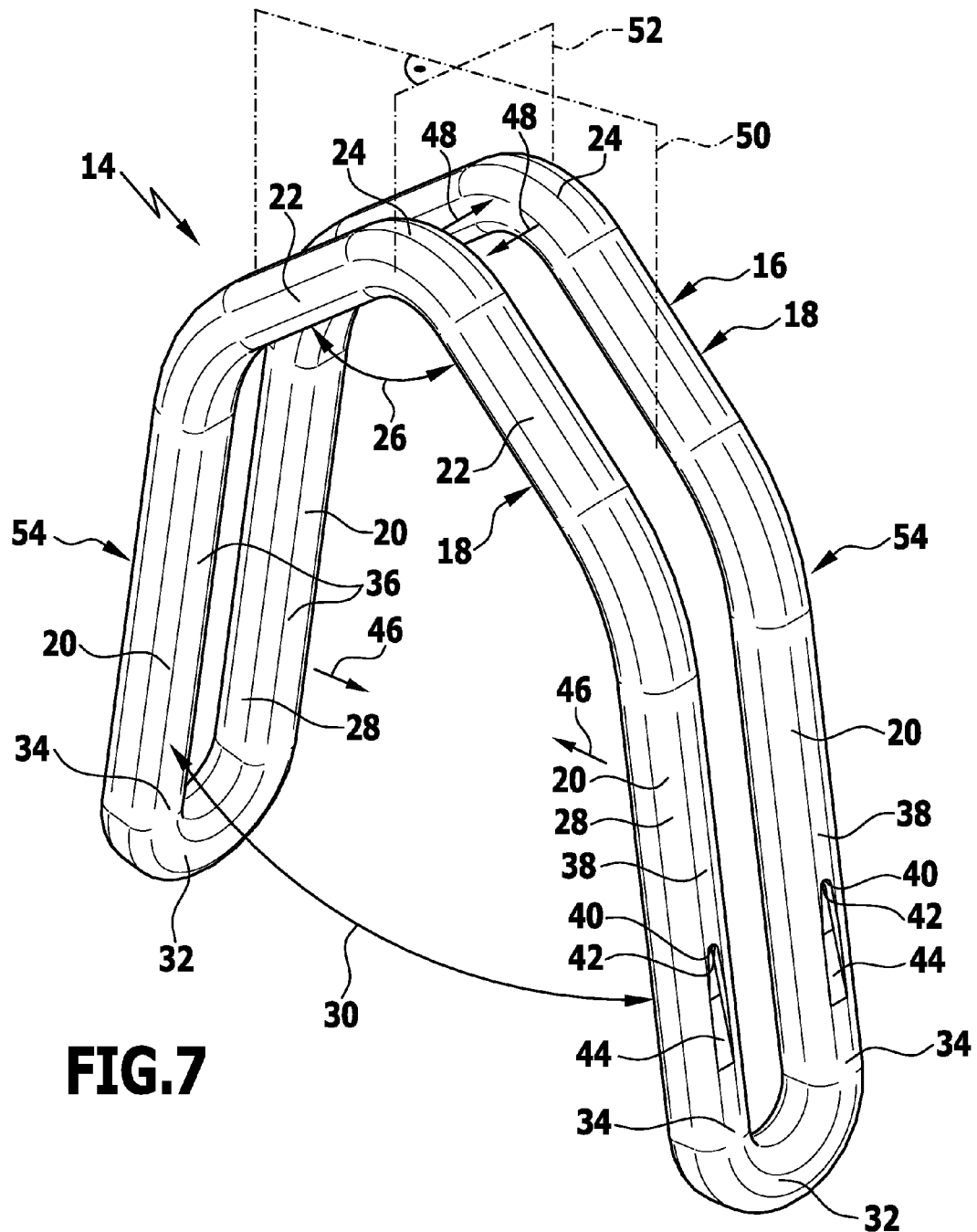
FIG. 7 shows an enlarged view of the surgical clip retained in a clip receptacle of the clip carrier device shown in FIG. 1.

The clip carrier device 10 and in particular the clip receptacles 12 thereof are preferably constructed to receive the clip 14, which is designed in the form of a so-called double-shank clip 16. The double-shank clip 16 is effectively formed by two simple, substantially C-shaped brackets 18, each comprising two retaining or clamping arms 20. Each retaining arm 20 defines two sections, a first section 22, which extends away from a connection point 24 of each bracket 18 between the two retaining arms 20, wherein in a basic position, as shown schematically in FIG. 7, the first sections 22 of the two retaining arms 20 define between them an aperture angle 26 which is preferably in a range between 70° and 140°. The first section extends away from the connection point 24 and merges into a second section 28, wherein the second sections 28 are inclined or bent relative to the first sections 22 in such a way that an aperture angle 30 defined between the second sections 28 is smaller than the aperture angle 26. The two brackets 18 are connected to one another by means of two connecting curves 32, each of which is joined to one of two free ends 34, which lie adjacent to one another, of the second sections 28 of the brackets 18 aligned parallel to one another.

Inner faces 36 in particular of the second sections 28 form clamping faces of the clip 14 which can be brought into a closed position in which they are permanently close together. Thus with the clip 14 it is possible for example to pinch off hollow organs, such as in particular blood vessels or bulges thereof in the form of aneurysms.

In order to improve handling of the clip 14, a recess 40 is constructed on each of the outside surfaces 38 of the second sections 28, wherein each recess comprises a stop face 42 facing in the distal direction and a sliding face 44 which rises in the distal direction from the stop face to the outer face 38 and is slightly inclined relative to the outer face 38. The recesses 40, which thus form tool element receptacles, make it possible in particular for a surgeon to grip the clip 14 firmly with an instrument (not shown more closely), wherein the instrument preferably has projections which are constructed corresponding to the recesses 40 and can engage therein.

A characteristic of the clip 14 is that a movement of the retaining arms 20 towards one another, that is to say in the direction of the arrows 46, leads to a permanent deformation of the connection point 24. On the other hand, due to the special design of the connecting curves 32 it is possible to move the brackets 18 in the region of the connection points 24 towards one another, i.e. in the direction of the arrows 48, or away from one another to a certain extent without a plastic deformation of the clip 14 occurring in the region of the connection curves 32. Thus in other words the clip 14 is resiliently deformable to a limited extent in a direction perpendicular to a first plane of symmetry 50 by which one bracket 18 of the clip 14 is reflected in the other bracket 18. On the other hand, in a plane of symmetry 52 which is perpendicular to the plane of symmetry 50 for the application of the clip 14 a plastic deformation is desirable in particular in the region of the connection point 24 and in the transition regions between the first portions 22 and the second portions 28.

Thus overall the double-shank clip 16 is constructed with two respective clip arms 54 which each comprise two retaining arms 20, oriented parallel to one another, of the retaining brackets 18 extending from the connection point 28, and a connecting curve 32.

The clip receptacle 12 to receive the clip 14 comprises two retaining arm receiving spaces which each serve to receive one clip arm 54. They are formed by recesses 58 of a basic body 60 of the clip carrier device 10. The basic body 60 has a planar underside 62, which is breached by the recesses 58 constructed in the form of openings in the base body. Thus the clip receptacles 12 are open at the bottom by an outlet opening 64.

Figure 3:
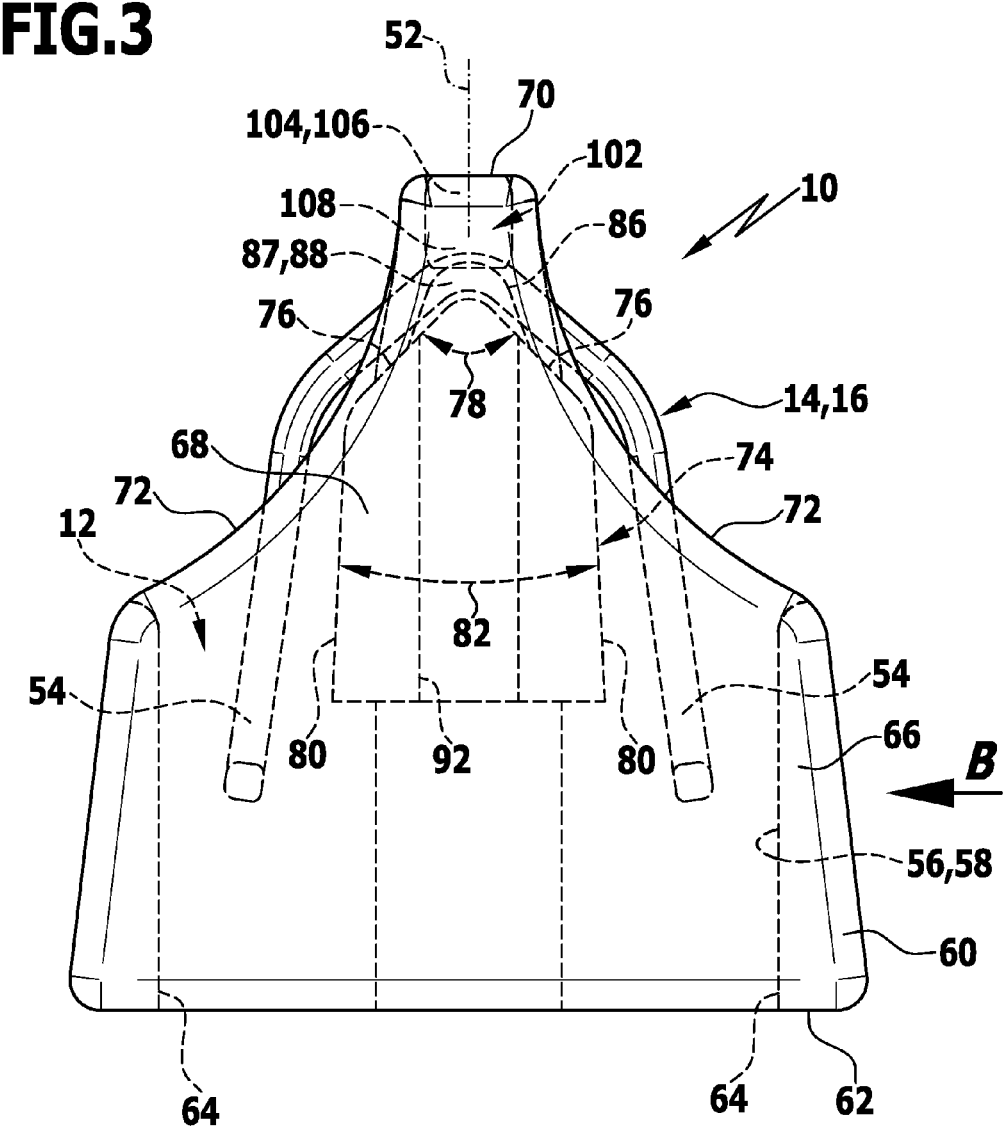
FIG. 3 shows a partially open side view of the clip carrier device according to FIG. 1 in the direction of the arrow A in FIG. 2.
Figure 4:
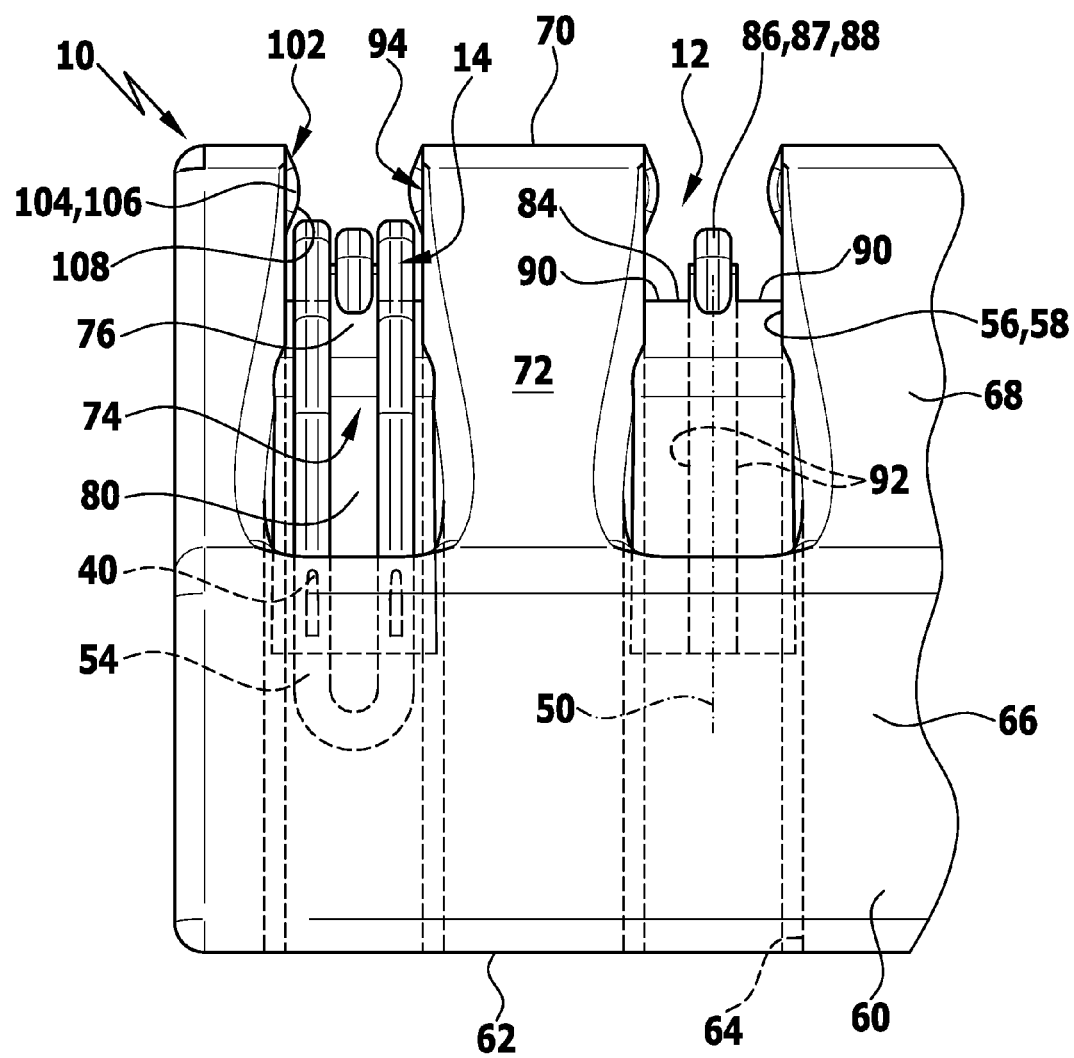
FIG. 4 shows a side view of the clip carrier device according to FIG. 1 in the direction of the arrow B in FIG. 3.

In a side view, as shown schematically in FIG. 3, the basic body 60 is constructed in the lower region in the form of a trapezoidal prism 66, and in the region lying above that, that is to say on an upper face of the prism 66, and directed away from the lower face 62, the basic body is constructed substantially in the form of a three-sided prism 68 with a stumpy upper side 70 extending parallel to the underside 62 as a flattened tip and with concave curved side faces 72 facing away from the basic body 60 on both sides. The side faces 72 are partially opened, which simplifies the introduction of the clip arms 54 with the connecting curves 32 onward into the retaining arm receiving spaces 56.

Figure 2:
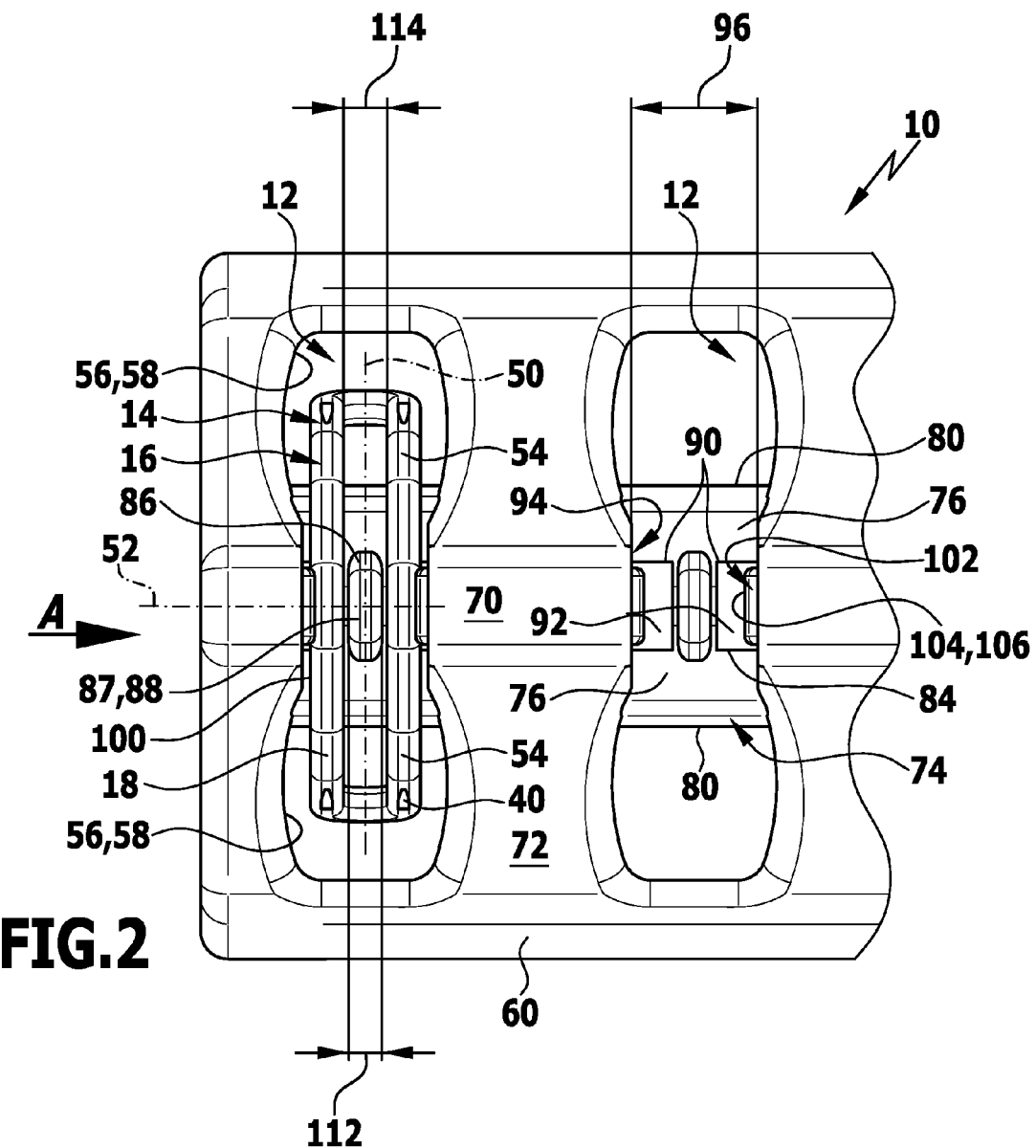
FIG. 2 shows an enlarged plan view of a detail of the clip carrier device shown in FIG. 1.

For mounting of the clips 14, in the interior of the clip receptacles 12 a bearing element 74 delimiting these at least in some sections is constructed symmetrically with respect to the planes of symmetry 50 and 52 and has two support surfaces 76 which are inclined relative to one another and face away from the basic body 60. An angle 78 enclosed between the support surfaces 76 is somewhat smaller than the aperture angle 26, at most equal to the aperture angle, so that inner faces 36 of the first sections 22 can abut against the support surfaces 76. The support surfaces 76 merge into adjoining inner faces 80 which are inclined with respect thereto and which enclose an angle 82 smaller than the aperture angle 30, so that the clip arms 54 protrude freely into the retaining arm receiving spaces 56, as shown schematically in FIGS. 2 and 3.

A contact surface 84 which extends substantially parallel to the underside 62 is constructed in the transition region between the support surfaces 76, and this contact surface is divided into two contact surface sections 90 by a separating element 86 in the form of a separating projection 87 which extends parallel to the plane of symmetry 50, projects from the contact surface 84 and can be formed as a rib 88 or can be ribbed. The contact surface sections 90 are each provided with an aperture in the form of a flushing opening 92.

An access from above, that is to say coming from the upper face 70, into the clip receptacle 12 is defined by an insertion opening 94. This defines a width 96 in a direction parallel to the plane of symmetry 52 which is somewhat greater than the spacing 98 of side faces, which face away from one another, of the brackets 18 in the region of the connection points 24 thereof. Thus due to its dimensions the insertion opening 94 would in principle enable the clip 14 to be inserted into the clip receptacle 12 without being deformed in any way. However, it could then also fall out of the clip receptacle, for example if the clip carrier device 10 is moved, in particular turned over, that is to say if in particular the upper face 70 were to form the lower face of the clip carrier device 10.

Figure 5:
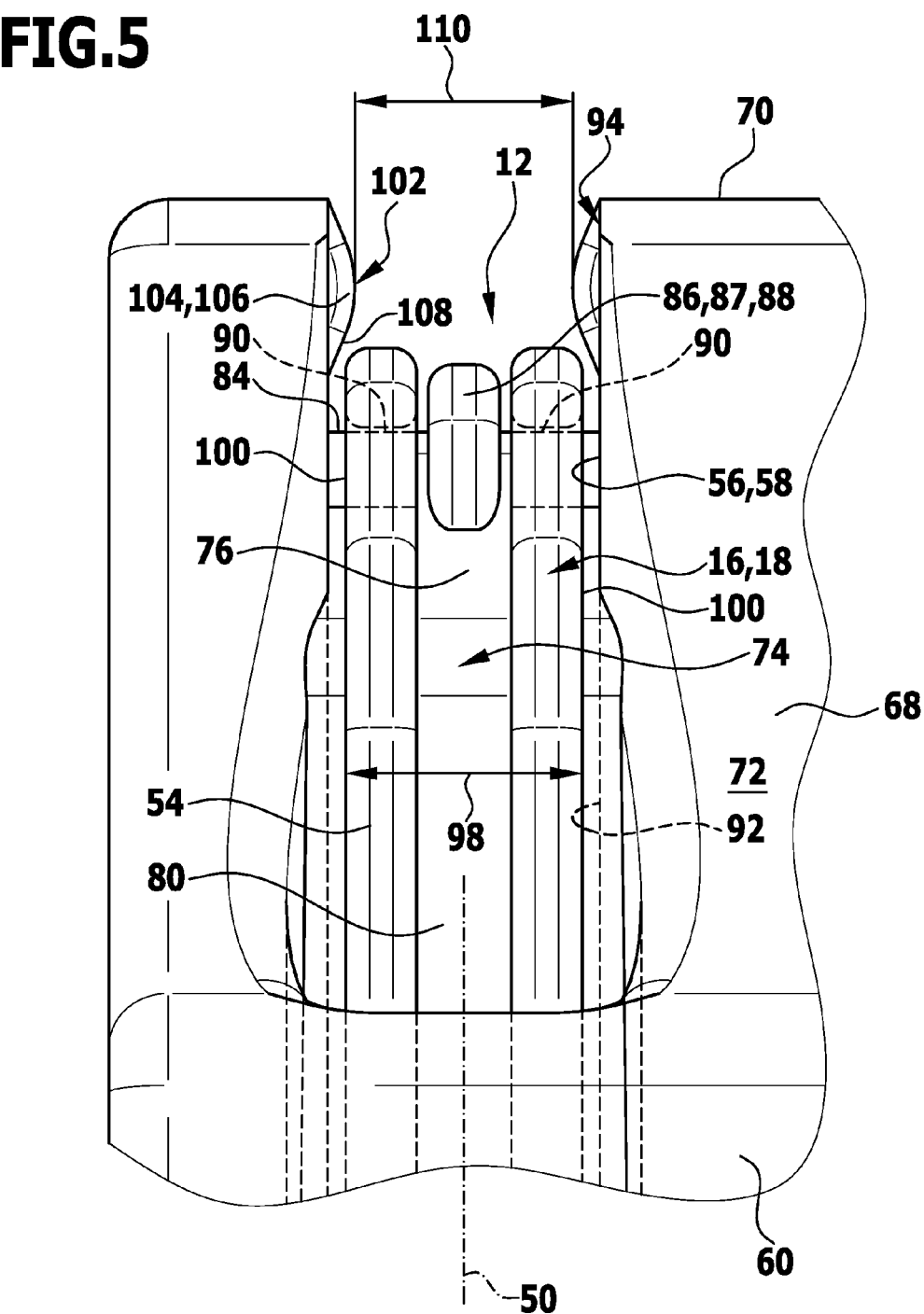
FIG. 5 shows an enlarged view of a detail of the clip carrier device shown in FIG. 4.
Figure 6:
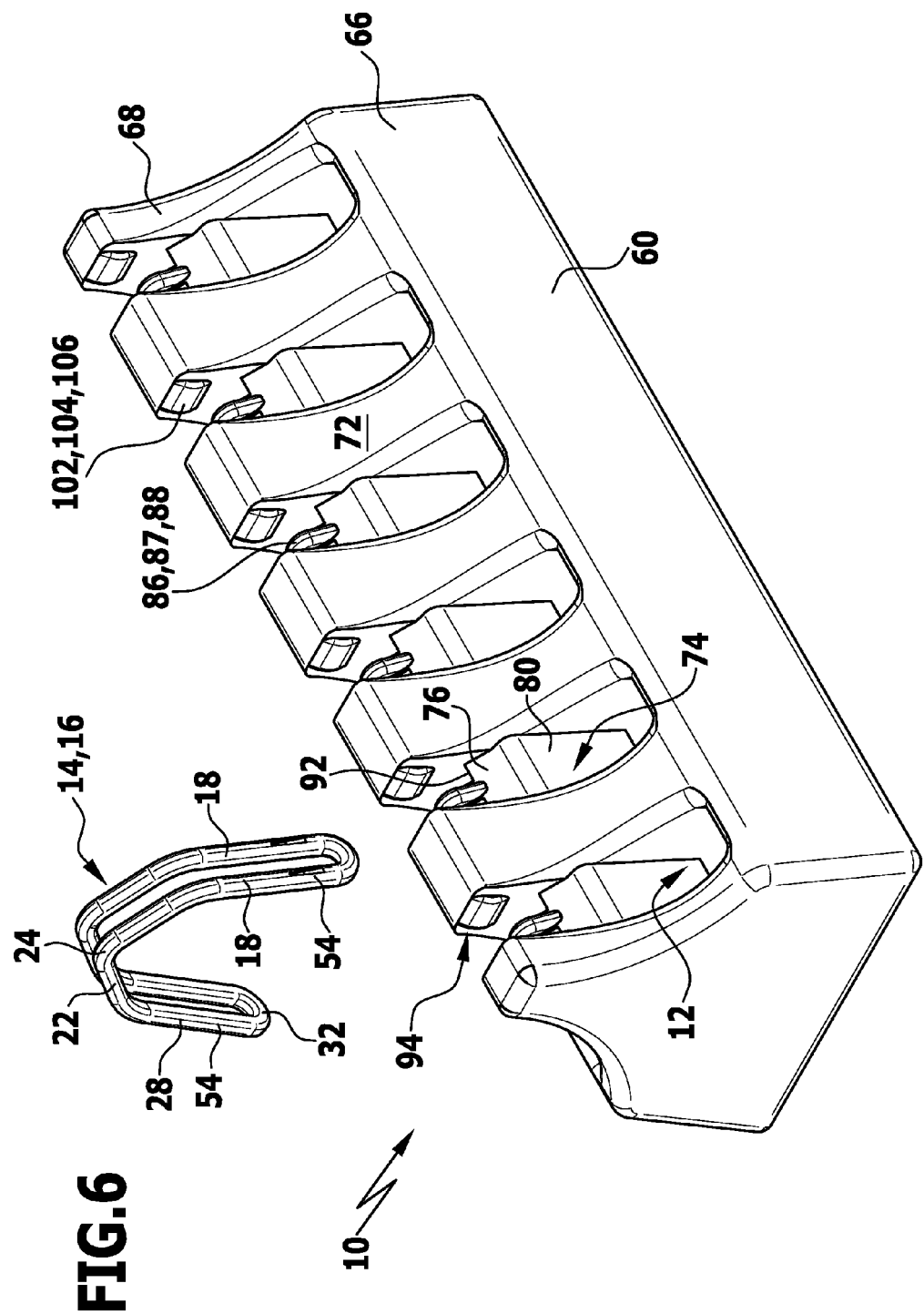
FIG. 6 shows a perspective view of the clip carrier device shown in FIG. 1 after removal of the clip.

A securing device 102 is provided in order to prevent a clip 14 from falling out unintentionally from a clip receptacle 12. This comprises at least one securing member 104. In the embodiment illustrated in the drawings two securing members 104 are provided which are constructed in the form of retaining projections 106 which partially protrude into the insertion opening 94. The securing members 104 each have a retaining face 108 facing in the direction or substantially in the direction into the clip receptacle 12. The securing members 104 are oriented facing one another and narrow the insertion opening 94. The spacing 110 between the securing members 104 is less than the spacing 98, so that the clip 14 must be deformed in the region of the connection points 24 by a movement of the brackets 18 towards one another in the region of the connection points 24, so that the connection points of the brackets 18 can pass the securing device 102 when the clip 14 is introduced into the clip receptacle 12. After the introduction of the clip 14 into the clip receptacle 12 the connection points spring outwards again, i.e. away from one another, so that the clip 14 is secured in the clip receptacle 12. A width 112 of the separating element 86 is adapted to a spacing 114 of the connection points 24 of the two brackets 18 from one another in the basic position of the clip 14, preferably somewhat less than the spacing 114, so that, as shown schematically in FIG. 5, the separating element 86 can penetrate between the two connection points 24, in particular without contact or at least without exertion of forces.

The clip 14 cannot come out of the clip receptacle 12 unaided, that is to say in particular without an extraction tool for extraction of the clip 14 from the clip carrier device 10. The clip is prevent from falling out by the retaining faces 108, against which the connection points 24 abut when the clip carrier device 10 is for example shaken or turned upside down.

For removal of the clip 14 from the clip carrier device 10 the clip is preferably gripped by a holding or insertion instrument which uses the recesses 40 provided in the outer faces 38. When the clip 14 is pulled back in a direction at right angles away from the upper face 70, that is to say when it is pulled out of the clip receptacle 12, the clip 14 is somewhat deformed in the region of the connection points 24, as already described above, as the brackets 18 are moved towards one another in the region of the connection points 24 in the direction of the arrows 48. In this way it is possible for the connection points 24 to pass the securing members 104. Since, when the clip 14 is removed from the clip receptacle 12, it is preferably gripped exclusively at the recesses 40, that is to say in the region of distal ends of the clip arms 54, the clip 14 can preferably be resiliently deformed in the necessary way solely due to the connection points 24 sliding on the retaining faces 108 and returns to its basic position shown schematically in FIG. 7 as soon as the connection points 24 have passed the securing members 104.

The clip 14 is preferably constructed in one piece and is produced from an implant material, for example titanium. The clip carrier device 10 is preferably also constructed in one piece. Consideration may be given here in particular to plastics materials, from which the clip carrier device 10 can be produced by injection moulding Plastics materials are preferably chosen which can be sterilised with steam and are also substantially inelastic. This makes it possible in particular to design the clip carrier device 10 without moving parts. Thus in particular the securing device 102 may be constructed exclusively by rigid, inelastic securing members 104. This simplifies the production of the clip carrier device 10 and increases the security of mounting of the double-shank clip 16.

The invention claimed is:

1. Medical clip carrier device for at least one of retention and mounting of at least one medical clip, comprising:
    at least one clip receptacle in which a clip is retainable in a mounted position, and
    a securing device with at least one securing member for detachably securing a clip in the at least one clip receptacle,
    each of the at least one clip receptacle comprising an insertion opening for insertion of a clip into a respective one of the at least one clip receptacle and removal of the clip therefrom,
    the at least one securing member comprising a retaining projection which protrudes at least partially into the insertion opening,
    wherein:
        each of the at least one clip receptacle comprises at least two support surfaces, against which, in the mounted position, a respective limb of a clip abuts at least in some sections or substantially abuts,
        the at least two support surfaces are connected to one another via a contact surface,
        the contact surface comprises at least one separating element for separating or dividing the contact surface into a first and a second contact surface section,
        the contact surface comprises at least one flushing opening,
        at least one medical clip is retained in the at least one clip receptacle, and
        the at least one medical clip comprises a double-shank clip.

2. Medical clip carrier device as claimed in claim 1, wherein the at least one securing member has a retaining face facing in a direction into the clip receptacle.

3. Medical clip carrier device as claimed in claim 2, the at least one securing member comprises at least two securing members.

4. Medical clip carrier device as claimed in claim 3, wherein the at least two securing members are oriented facing one another and narrow the insertion opening.

5. Medical clip carrier device as claimed in claim 1, wherein each of the at least one clip receptacle is constructed symmetrically with respect to at least one mirror plane.

6. Medical clip carrier device as claimed in claim 1, wherein each of the at least one clip receptacle comprises two retaining arm receiving spaces to receive a respective retaining arm of the clip.

7. Medical clip carrier device as claimed in claim 1, wherein the contact surface is constructed facing in a direction of the insertion opening.

8. Medical clip carrier device as claimed in claim 1, wherein the at least one separating element comprises a separating projection projecting from the contact surface.

9. Medical clip carrier device as claimed in claim 8, wherein the at least one separating element is ribbed or constructed in the form of a rib.

10. Medical clip carrier device as claimed in claim 6, wherein the at least one separating element defines a first plane of symmetry which reflects each of the two retaining arm receiving spaces in itself.

11. Medical clip carrier device as claimed in claim 6, wherein the at least one separating element defines a second plane of symmetry which reflects the at least one separating element in itself and reflects one of the two retaining arm receiving spaces into the other of the two retaining arm receiving spaces and vice versa.

12. Medical clip carrier device as claimed in claim 1, wherein:
    the at least one flushing opening comprises two flushing openings, and
    the at least one separating element separates the two flushing openings from one another.

13. Medical clip carrier device as claimed in claim 1, further comprising at least one outlet opening arranged in a bottom of the clip receptacle.

14. Medical clip carrier device as claimed in claim 6, wherein each retaining arm receiving space has at least one partially open side face facing away from the clip carrier device.

15. Medical clip carrier device as claimed in claim 1, wherein the clip carrier device is constructed in one piece.

16. Medical clip carrier device as claimed in claim 1, wherein the clip carrier device comprises no moving parts.

17. Medical clip carrier device as claimed in claim 1, wherein the securing device comprises exclusively rigid, inelastic parts.

18. Medical clip carrier device as claimed in claim 1, wherein each of the at least one clip receptacle is equipped with a medical clip.

19. Medical clip carrier device as claimed in claim 1, wherein:
    the at least one medical clip comprises two retaining arms which are connected to one another at each end via a deformable connection point and are bendable towards one another in such a way that the retaining arms are moveable out of an open position in which they have a greater spacing from one another into a closed position in which inner faces, which face towards one another, of the retaining arms are permanently moved close together, and
    a spacing between side faces, which face away from one another, of the at least one separating element is smaller than a spacing between inner side faces, which face one another, of the retaining arms in the region of the connection point.

* * * * *